United States Patent [19]
Gregory

[11] Patent Number: 4,913,683
[45] Date of Patent: Apr. 3, 1990

[54] INFUSION STENT SYSTEM

[75] Inventor: Franklin P. Gregory, Racine, Wis.

[73] Assignee: Medical Engineering Corporation, Racine, Wis.

[21] Appl. No.: 215,077

[22] Filed: Jul. 5, 1988

[51] Int. Cl.⁴ .............................................. A61M 25/00
[52] U.S. Cl. ....................................... 604/8; 604/281
[58] Field of Search ...................................... 604/8–10, 604/34, 43, 281, 282

[56] References Cited

U.S. PATENT DOCUMENTS

| | | | |
|---|---|---|---|
| 4,610,657 | 9/1986 | Densow | 604/8 |
| 4,787,884 | 11/1988 | Goldberg | 604/8 |
| 4,813,925 | 3/1989 | Anderson et al. | 604/8 |

Primary Examiner—Dalton L. Truluck
Attorney, Agent, or Firm—Stuart E. Krieger

[57] ABSTRACT

The infusion stent system includes a stent member having a plurality of openings provided in the wall of the stent along the entire length of the stent. An imperforate open ended guide tube member used for installation and infusion of the stent accommodates a core member that stiffens the guide tube member. The core member is relatively moveable in the guide tube member to provide selective flexibility at a proximal end of the guide tube member. The stent is positioned in the renal cavity, the ureter and bladder by being pushed along the guide tube member by a push catheter. Fluid is infused through a proximal end of the guide tube member when the core member is removed. The proximal end of the guide tube member can be located at any selected position within the stent. Thus fluid can be infused to any selected location in the stent by positioning the proximal end of the guide tube member at a desired location in the stent. Openings in the stent that are bypassed by the guide tube member are not infused with fluid.

24 Claims, 4 Drawing Sheets

INFUSION STENT SYSTEM

BACKGROUND OF THE INVENTION

This invention relates to ureteral stents, and more particularly to a novel infusion stent system that permits infusion of fluid at any selected location in the stent.

Ureteral stents have long been used for such purposes as draining fluid from the renal pelvis to the bladder, and for providing support to a collapsed or restricted ureter.

Ureteral stents may also be used in conjunction with extracorporeal shock wave lithotropsy (ESWL), a procedure for pulverizing kidney stones without surgery. During ESWL, a device known as a lithotripter emits high frequency electrohydraulic waves that destroy the kidney stones. The waves are administered to a patient submerged in a bath of water. Electrodes are attached to brass disk behind the patient and when the lithotripter is activated, up to 1500 electrohydraulic waves travel through the water to crush the stone to infinitesimal fragments that the patient can then pass naturally. The natural passing of the stone is facilitated with a stent.

One known stent used in ESWL procedures, designated the Kwart Retro-Inject Stent manufactured by Cook Urological of Spencer, Ind., and identified by Model Nos. 003600 and 003700, includes a system comprising a stent, a solid core wire guide, an inserter and a release sleeve. The stent is normally coiled or looped at opposite ends and includes perforations along the length of the stent.

In using the Kwart Retro-Inject Stent Set, the wire guide is positioned in the patient and the stent is pushed on the wire guide into the renal cavity by the inserter. The inserter is pushed into the stent a distance of approximately 5 mm thus forming a tubular extension of the stent.

After the stent is positioned in the patient, the wire guide is removed to allow the stent coils or loops to re-form in the renal pelvis. Fluid is injected through the inserter and into the stent during an ESWL procedure to disclose stones or stone fragments for targeting. The stent can also be left in place for internal drainage.

One of the problems with the Kwart Retro-Inject stent system is that infusion of fluid through the inserter cannot be specifically directed outwardly of the stent at any selected portion of the stent. Fluid is injected into one end of the stent through the inserter. The injected fluid traverses the stent exiting through any or all of the openings in the stent.

Another known stent set manufactured by Cook Urological under the designation Wegenke Exchange/Retrograde Ureteral Stent Set Model No. 0046, is also unable to direct fluid to any selected part of the stent. Fluid injected into one end of the stent traverses the stent to whatever openings are provided therein.

Still another known stent set made by Van-Tec of Spencer, Ind., under Model No. SI1726, also requires injection of fluid through one end of the stent for passage within the stent to any available openings in the stent or an open end of the stent. Since fluid can only be injected through an end of the stent, fluid infusion cannot be focused outwardly of the stent at any one location in the stent if openings are distributed along the length of the stent.

It is thus desirable to provide an infusion stent system which can be used to infuse fluid at any selected location in a stent and which also has optimal drainage capability when the stent is left as an indwelling member.

OBJECTS AND SUMMARY OF THE INVENTION

Among the several objects of the invention may be noted the provision of a novel infusion stent system, a novel infusion stent system which permits fluid to be infused into the stent at any selected location in the stent, a novel infusion stent system which permits fluid to be infused outwardly of a stent at selected locations in the stent and also permits maximum drainage of fluid into the stent when the stent is left as an indwelling member, a novel infusion stent system which includes an adjustable bypass member that bypasses openings in the stent to direct outward infusion of fluid from the stent beyond such bypassed openings, and a novel method of infusing fluid in the renal cavity.

Other objects and features of the invention will be in part apparent and in part pointed out hereinafter.

In accordance with the present invention, the infusion stent system includes a flexible stent member having a main body portion with a normally curved proximal end portion and a normally looped distal end portion. Openings can be provided in the wall of the stent along the entire length thereof including the main body portion and the proximal and distal end portions.

The system further includes a hollow, flexible guide tube member open at opposite ends and having an imperforate wall. The stent member is sized to be drawn over the guide tube member for relative slidable movement between the stent member and the guide tube member.

A flexible core member is slidably received in the guide tube member to stiffen the guide tube member. The core member has an enlarged portion at one end to limit insertion in the guide tube member and a terminal portion at the opposite end. The terminal portion has a reduced cross-section relative to the cross-section of a main body portion of the core member. A free end of the core member adjacent the terminal portion has an enlargement that is of greater magnitude in cross-section than the terminal portion but of lesser magnitude in cross-section than the main body portion.

The core member can be selectively retracted from the guide tube member to provide varying degrees of flexibility of the guide tube member at a proximal end portion thereof.

The infusion stent system further includes a push catheter member that is also drawn onto the guide tube member for relative slidable movement between the push catheter member and the guide tube member.

Location of the infusion stent system in a patient usually begins with full engagement of the core member in the guide tube member. The stent member is drawn onto the guide tube member after the core member has been positioned in the guide tube member.

The flexibility of the core member and the guide tube member are selected so as to enable the normally curled proximal end portion and the normally coiled distal end portion of the stent to substantially straighten when drawn onto the guide tube member and core member combination.

It should be noted that the guide tube member by itself is too flexible to straighten the curled proximal end and coiled distal end portions of the stent member. Thus when the core member is withdrawn from the guide tube member while the stent member is disposed on the guide tube member, the curled proximal end portion and the coiled distal end portion will tend to reform.

Before the stent member is positioned in the renal cavity, the ureter and the bladder, the guide tube member and core member are positioned therein. The stent member is urged along the guide tube member and core member combination into the bladder, the ureter and the renal cavity by movement of the push catheter along the guide tube member against the distal end portion of the stent.

Once the stent member has been adequately positioned in the renal cavity, the ureter and the bladder, the core member can be removed from the guide tube member, enabling the curved proximal end portion and the coiled distal end portion of the stent member to reform in the renal cavity and the bladder. Removal of the core member opens an infusion channel through the guide tube member into the stent.

If the proximal end of the guide tube member is located at the proximal end portion of the stent member, infusion can be directed into the renal cavity. Since the wall of the guide tube member is imperforate, openings in the stent member that are bypassed by the proximal end of the guide tube member are generally not infused with fluid from the guide tube member.

The guide tube member can be retracted from the proximal end of the stent member toward the distal end of the stent member to locate the proximal end of the guide tube member in any selected position relative to the stent member. Thus, location of the proximal end of the guide tube member in the main body portion of the stent will permit infusion of fluid in the ureter as well as the renal cavity. Location of the proximal end of the guide tube member at the distal end of the stent will permit infusion to take place through openings provided along the entire length of the stent.

When the infusion process is completed, the guide tube member can be removed from the stent member. The stent member can then be left as an indwelling member and furnishes optimal drainage capability because of the provision of openings along the entire length of the stent.

Sutures provided at a distal end of the stent member extend outwardly of a patient to permit nonsurgical removal of the stent member when such removal is desired.

The invention accordingly comprises the constructions and method hereinafter described, the scope of the invention being indicated in the claims.

DESCRIPTION OF THE DRAWING

In the accompanying drawings.

Corresponding reference characters indicate corresponding parts throughout the several views of the drawings.

DETAILED DESCRIPTION OF THE INVENTION

Figures 1, 2:
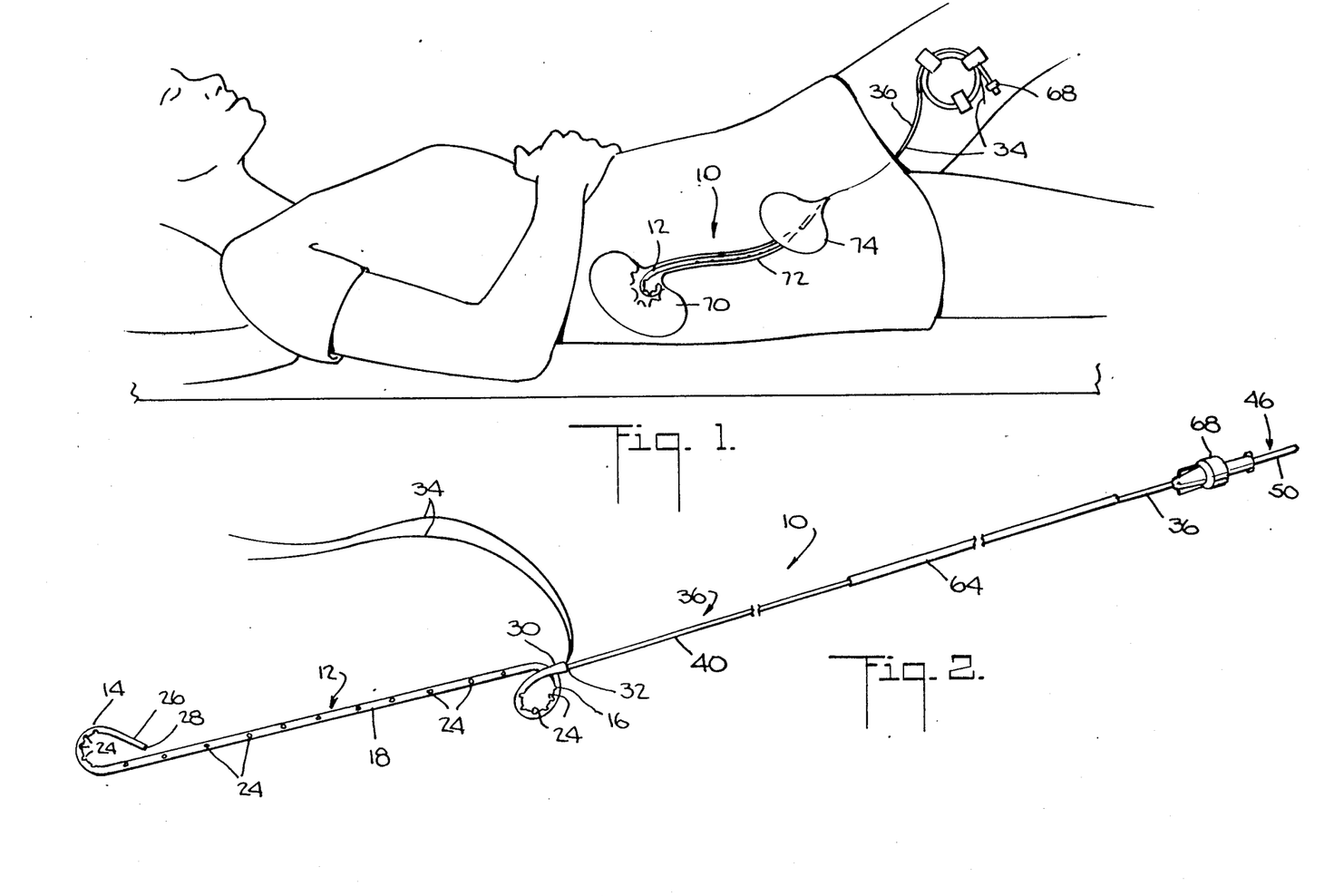
FIG. 1 is a simplified schematic view of the infusion stent system in a patient.
FIG. 2 is a simplified perspective view thereof.

An infusion stent system incorporating one embodiment of the invention is generally indicated by the reference number 10 in FIGS. 1 and 2.

The ureteral stent system 10 includes a stent member 12 having a normally curl-shaped proximal end portion 14, a normally loop-shaped distal end portion 16 and a elongated main body section 18 intermediate the proximal and distal end portions 14 and 16.

The stent 12, which is formed of a soft, flexible, biocompatible material such as silicone, has a generally tubular wall 20 with an internal passageway or lumen 22. A plurality of openings 24 are provided in the wall 20 at the proximal and distal end portions 14 and 16, and in the main body section 18. The proximal end portion 14 has a tapered or reduced free end 26 which is open at 28. The distal end portion 16 has a slightly flared free end 30 which is open at 32. A suture 34 attached to the distal end portion 16 extends from the opening 32.

Figure 6:
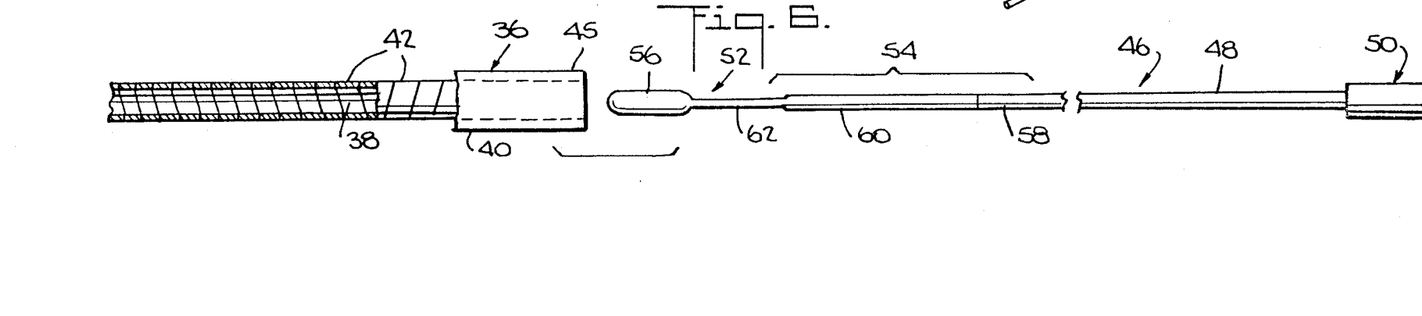
FIG. 6 is an enlarged fragmentary detail, partly shown in section, of the guide tube member and core member thereof.

The system 10 further includes an elongated, hollow, open ended, flexible guide tube member 36 which the stent member 12 can slidably accommodate. Referring to FIG. 6, the guide tube member 36 has an internal passageway or lumen 38 and an imperforate wall 40. The guide tube member 36 is preferably formed of a fluorinated polymer material such as Teflon, reinforced with stainless steel wire. Preferably, the stainless steel wire is a flat, rectangular, Teflon coated wrap.

Figures 8, 9:
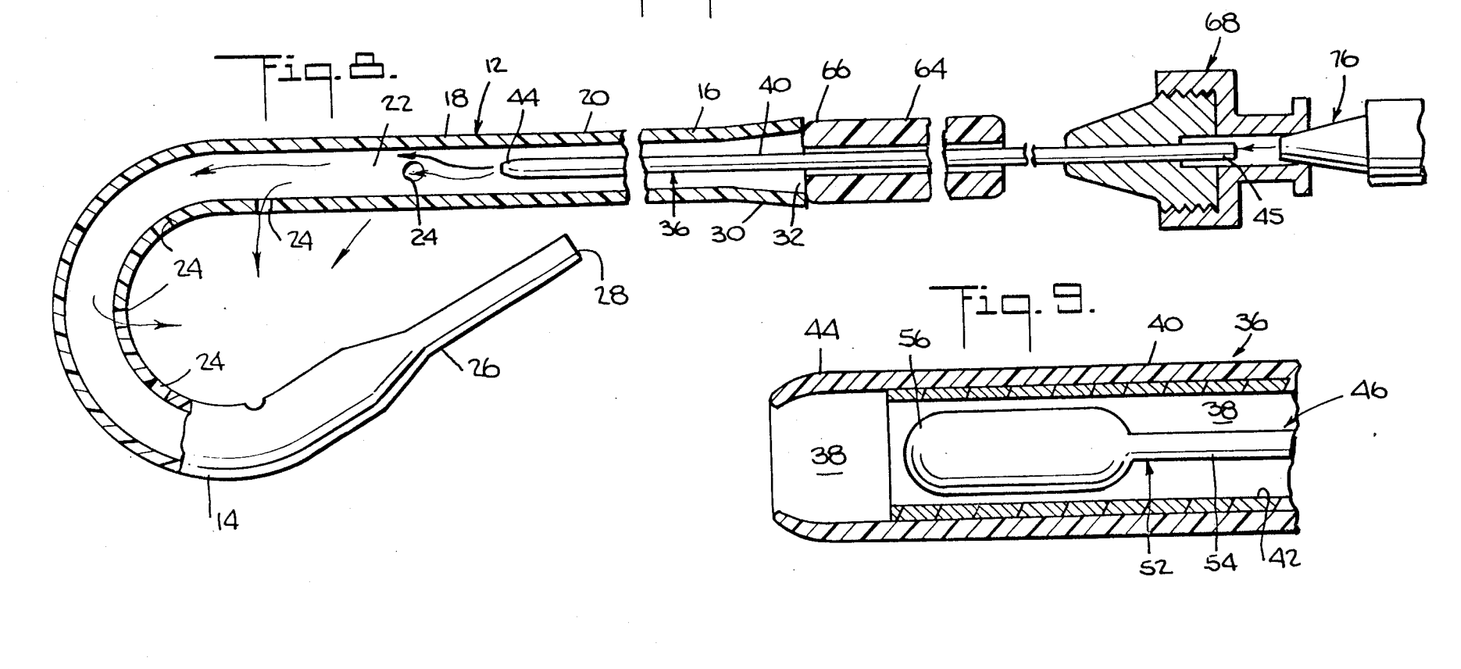
FIG. 8 is an enlarged fragmentary sectional view thereof during infusion, with the core member removed therefrom.
FIG. 9 is an enlarged fragmentary view, partly shown in section, of the proximal end of the guide tube member and the core member thereof.

Referring to FIG. 8, the wire reinforcement 42 can be terminated before a proximal end 44 of the guide tube member 36 enabling the proximal end 44 to be slightly reduced as shown in FIG. 9. The guide tube member also includes an opposite distal end 45.

A flexible, elongated core member 46, preferably formed of stainless steel, is slidably insertable in the guide tube member 36 and includes a main body portion 48, an enlarged distal end portion 50 and a proximal end portion 52. The enlarged distal end portion 50 is sized to be nonreceivable in the guide tube member 36 to limit insertion of the core member 46 in the guide tube member 36.

The main body portion 48 has a substantially uniform cross-sectional magnitude that permits slidable reception in the guide tube member 36. The proximal end portion 5 of the core member 46 has a reduced terminal section 54 of lesser cross-sectional magnitude than the main body portion 48. An enlargement 56 formed a the free end of the proximal end portion 52 joins the terminal section 54. The enlargement 56 is of greater cross-sectional magnitude than the terminal section 54 and substantially equivalent in cross-sectional magnitude to the main body portion 48. The terminal section 54 is progressively reduced toward the enlargement 56, as for example by reduced steps 58, 60 and 62 or by a continuous tapering toward the enlargement 56.

Figure 7:
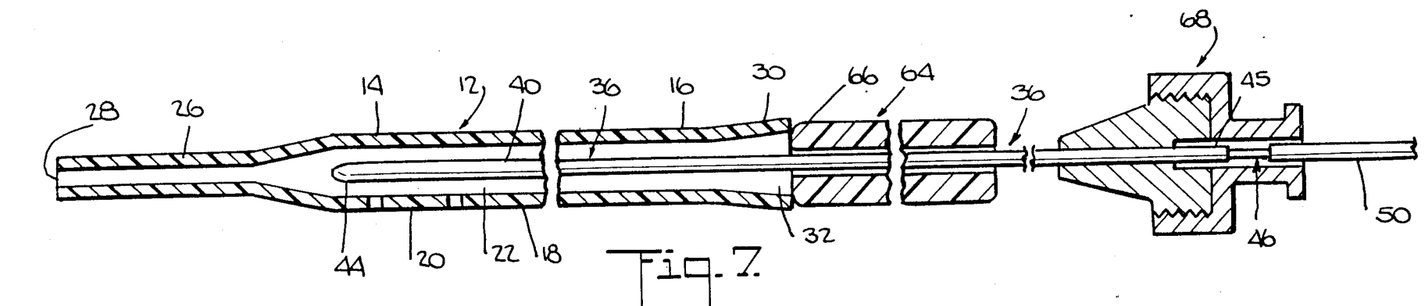
FIG. 7 is an enlarged fragmentary sectional view thereof with the guide tube member and core member positioned in the stent.

A flexible, tubular push-catheter member 64, formed of a suitable biocompatible polyethylene material, is slidably accommodated on the guide tube member 36. As shown in FIGS. 7 and 8, a proximal end 66 of the catheter member 64 is sized to butt against the distal end 16 of the stent member 12. Preferably the combined length of the stent member 12 and the push-catheter member 64 is less than the length of the guide tube member 36.

The precise dimensions of the stent system 10 may vary based on the dimensional characteristics of particular patients. Nevertheless, to exemplify the magnitudes being dealt with, the outside diameter of the stent can range from 2.0 to 2.8 mm. The inside diameter of the stent can range from 1.3 to 1.8 mm. The length of the stent can range from 12 to 30 cm. The openings in the stent can be provided approximately every 2 cm. along the main body of the stent and have a diameter of approximately 1.3 mm. The proximal and distal end portions of the stent would also contain openings spaced at approximately 0.8 cm. However such openings would be of a larger diameter such as 2.2 mm. The sutures 34 can have a 75 cm. trail from the stent.

The guide tube member 36 can have an outside diameter of approximately 0.965 mm. and an inside diameter of approximately 0.635 mm. The length of the guide tube member 36 can be approximately 148 cm.

The core member 46 can have an overall length of approximately 147.5 cm. from the enlarged distal end portion 50 to the enlargement 56 at the free end of the proximal end portion 52. The enlargement 50 can be approximately 44.5 mm. long with an outside diameter of approximately 0.965 mm. The terminal section 54 and enlargement 56 can be approximately 10.2 cm. long with the enlargement being approximately 1.22 mm. long and 0.457 mm. in diameter. The final core diameter before the enlargement 56 is approximately 0.178 mm.

The push catheter 64 can have an overall length of approximately 70 cm. with an inside diameter of approximately 1.2 mm. and an outside diameter of approximately 2.9 mm.

Figures 3, 4, 5:
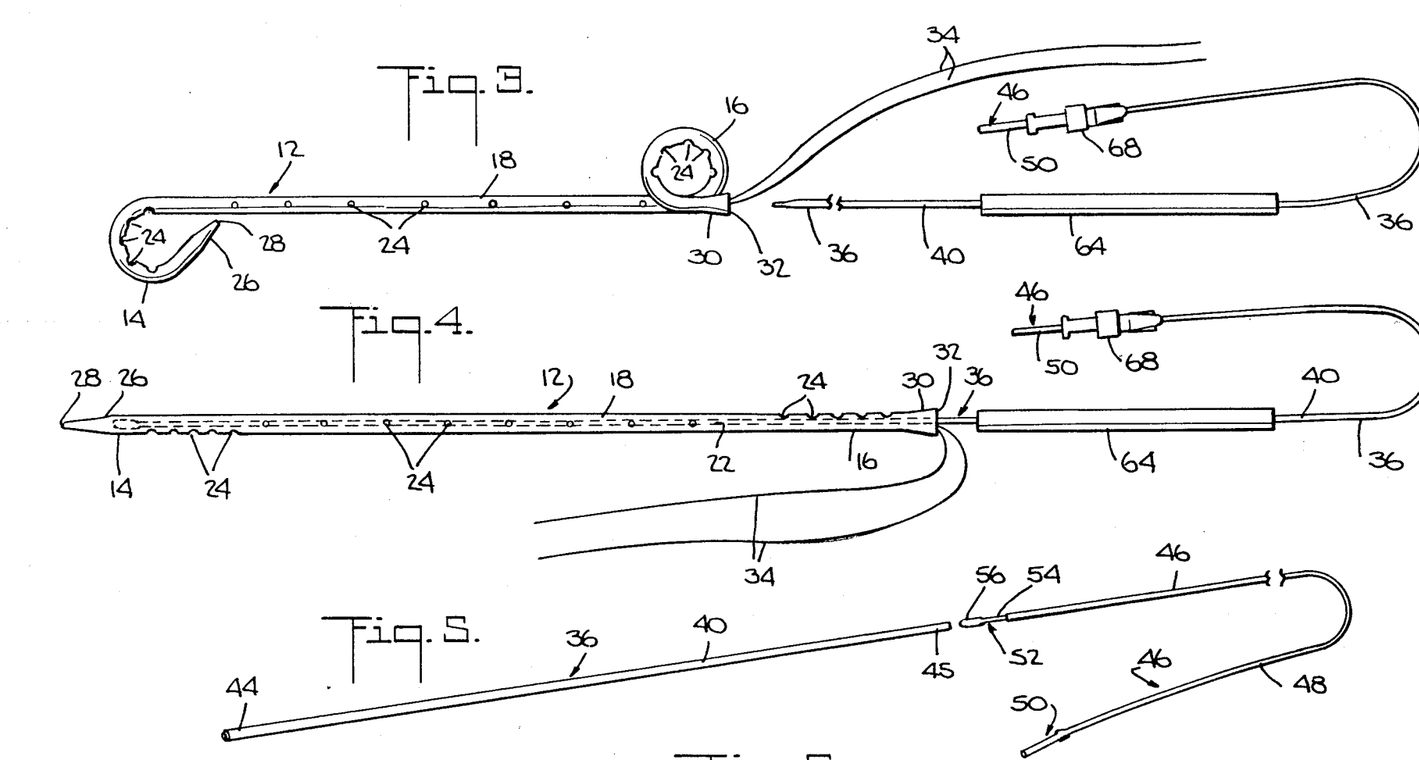
FIG. 3 is a side view thereof prior to straightening of the stent member.
FIG. 4 is a view similar to FIG. 3 after the stent member has been straightened.
FIG. 5 is a simplified schematic view of a guide tube member and a core member thereof.

In using the stent system 10 for fluid infusion, the core member 46 is inserted in the guide tube member 36 in the manner shown in FIG. 5. Thus, the enlargement 56 at the proximal free end of the core member 46 is inserted into the distal end 45 of the guide tube member 36 until the enlarged distal end portion 50 of the core member 46 abuts the distal end 45 of the guide tube member 36.

The guide tube member 36 and the core member 46 are sized such that the enlargement 56 at the proximal free end of the core member 46 does not project beyond the proximal end 44 of the guide tube member 36 when the enlarged distal end portion 50 of the core member 46 abuts the distal end 45 of the guide tube member 36. The desired relationship between the enlargement 56 at the proximal free end of the core member 46 and the proximal end 44 of the guide tube member 36, when the core member 46 is fully inserted in the guide tube member 36, is shown in FIG. 9.

The stent member 12 is drawn over the proximal end 44 of the guide tube member 36 and core member 46 combination. Drawing of the stent member 12 on the guide tube member 36-core member 46 combination serves to substantially straighten the normally curl-shaped proximal end portion 14 and the normally loop-shaped distal end portion 16 of the stent 12 in the manner shown in FIG. 4.

The push catheter 64 is likewise drawn onto the guide tube member 36 either before or after the stent 12 is in place on the guide tube member 36 to provide the arrangement shown in FIG. 4.

A luer hub 68 of any suitable known structure such as a Touhy Borst luer lock is joined to the distal end 45 of the guide tube member in the manner shown in FIG. 7.

The stent member 12 and the push catheter 64 are slid along the guide tube member toward the luer hub 68 to expose a predetermined length of the guide tube member 36 starting from the proximal end 44.

Figure 10:
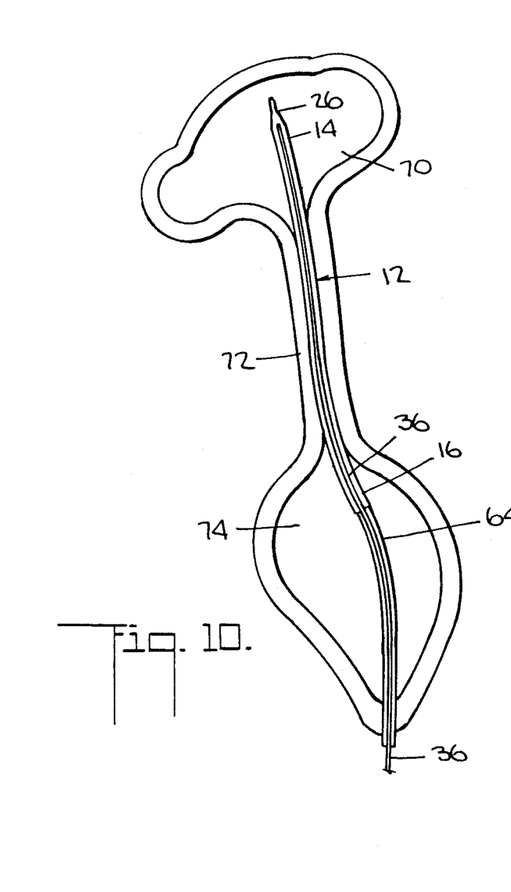
FIG. 10 is a simplified schematic view thereof during initial installation in the renal cavity, the ureter and the bladder.
Figure 11:
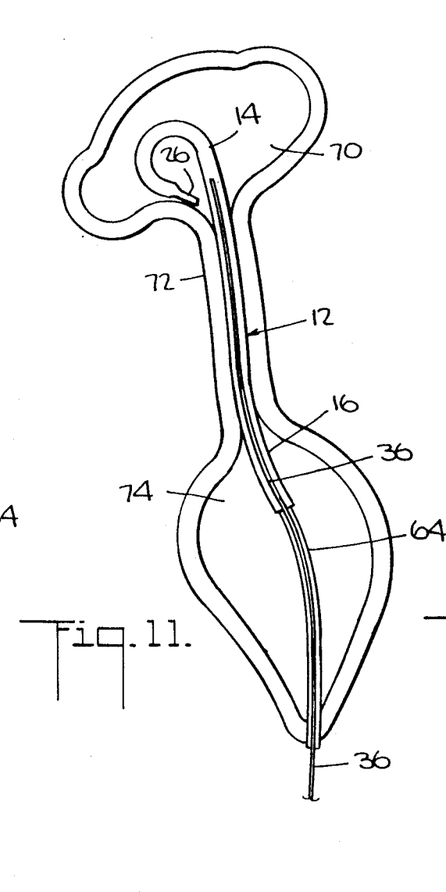
FIG. 11 is a view similar to FIG. 10 with the core member partially retracted from the guide tube member; and, FIG. 12 is a view similar to FIG. 10 with the core member and guide tube member entirely removed from the stent member.

The guide tube member 46 is then positioned in a patient using known techniques such that the proximal end portion 44 of the guide tube member 36 is located in the renal cavity 70 (FIG. 10). The remaining length of the guide tube member 36 extends through the ureter 72, the bladder 74 and externally of the patient.

It should be noted that the negotiation or positioning of the guide tube member 36 and core member 46 combination in the renal cavity 70, the ureter 72 and bladder 74 is facilitated by selectively retracting the core member 46 from the guide tube member 36 predetermined amounts to enhance the flexibility of the proximal end 44 of the guide tube member 36. Thus, a selective shifting of the core member 46 within the guide tube member 36 by manipulation of the enlarged distal portion 50 enables the proximal end portion of the guide tube member 36 to be softened or stiffened a needed to aid in negotiating movement of the guide tube member 36 and core member 46 combination through the ureter.

The reduced terminal section 54 of the core member 46 affords the guide tube member 36 a greater flexibility at the proximal end portion 44 than at the distal end portion 45. The flexibility of the proximal end portion 44 of the guide tube member 36 is further enhanced by retracting the core member 46 from the proximal end 44 of the guide tube member 36 to further aid in negotiating movement of the guide tube member 36 through the ureter 72.

After the guide tube member 36 and core member 46 combination have been adequately located in the renal cavity 70, the ureter 72 and the bladder 74, the stent member 12 can be positioned in the renal cavity 70, the ureter 72 and the bladder 74 by the push catheter 64. In accordance with known techniques, the proximal end 66 of the push catheter 64 is urged against the distal end 16 of the stent member 12 for movement of the stent member 12 along the guide tube member 36 to the desired position in a patient. The stent member 12 retains a substantially straightened configuration, such as shown in FIG. 10, during movement on the guide tube member 36.

When the proximal end portion 14 of the stent member 12 is adequately located in the renal cavity 70, the core member 46 can be withdrawn from the guide tube member 36 by maintaining the proximal end 66 of the push catheter 64 against the distal end 16 of the stent 12 and withdrawing the core member 46. As the core member 46 is withdrawn, the normally curl-shaped proximal end portion 14 of the stent member 12 substantially reforms, overcoming any restraint imposed by the presence of the guide tube member 36 in the stent member 12.

Figure 12:
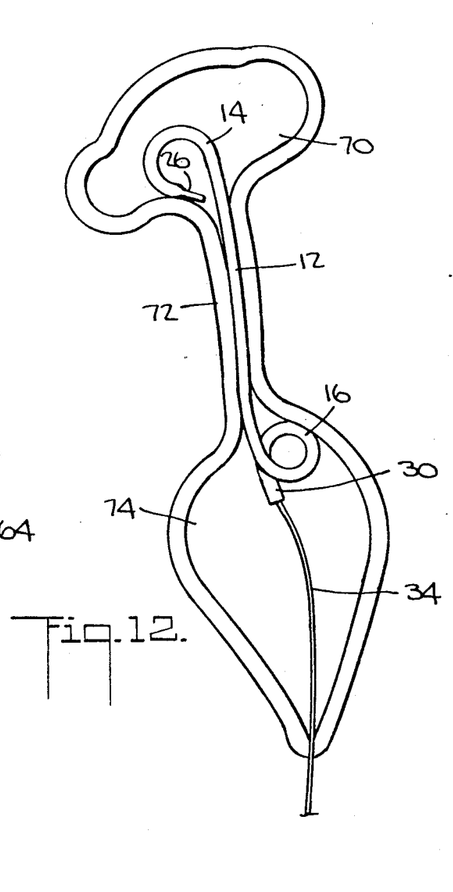

Complete withdrawal of the core member 46 from the guide tube member 36 enables the normally loop-shaped distal end portion 16 of the stent 12 to reform in the manner shown in FIG. 12. The loop-shaped distal end portion 16 of the stent 12 substantially reforms against any restraints due to the presence of the guide tube member 36 in the stent member 12.

Thus the guide tube member 36 by itself is insufficient to maintain the proximal and distal end portions of the stent member 12 in a straightened condition. The presence of the core member 46 in the guide tube member 36 provides the necessary restraint to straighten the proximal and distal end portions 14 and 16 of the stent 12 during positioning in a patient.

During and after installation of the stent 12 in a patient the sutures 34 are directed alongside the push catheter 64 and extend outside the patient.

To infuse fluid to the stent 12, a syringe 76 or any other suitable source of fluid is connected to the luer hub 68. Fluid is thus injected through the lumen 38 of the guide tube member 36. Since the wall 40 of the guide tube member 36 is imperforate, any fluid infused through the distal end 45 of the guide tube member 36 will exit through the proximal end 44 of the guide tube member 36. Thus the location of the proximal end 44 of the guide tube member 36 in the stent 12 determines the point at which fluid will be distributed outwardly of the stent 12.

For example, if the proximal end 44 of the guide tube member is located at the proximal end portion 14 of the stent 12 as shown in FIG. 8, the fluid infused through the guide tube member 36 will disperse through the openings 24 in the stent that are located beyond the proximal end 44 of the guide tube member 36.

The openings 24 in the stent member 12 that are bypassed by the proximal end 44 of the guide tube member 36 generally do not disperse fluid infused through the guide tube member 36.

The guide tube member 36 thus functions as an infusion channel and an adjustable bypass member. Accordingly, the guide tube member 36 directs fluid outwardly of the stent through openings beyond any selected location in the stent.

If it is desired to infuse fluid outwardly of the stent in an area starting in the ureter, the guide tube member 36 is retracted from the proximal end 14 of the stent 12. Such retraction is accomplished by maintaining the proximal end 66 of the push catheter 64 against the distal end 16 of the stent 12 and withdrawing the guide tube member 36 a predetermined amount to position the proximal end 44 of the guide tube member 36 at a selected location within the stent 12.

The positioning of the proximal end 44 of the guide tube member 36 at a selected relative position within the stent 12 is accomplished using known monitoring techniques. Since there is sufficient clearance between the stent 12 and guide tube member 36, the relative adjustment of the two components is easily accomplished.

As the guide tube member 36 is retracted from the proximal end 14 toward the distal end 16 of the stent 12, the openings 24 in the stent 12 that were previously bypassed by the guide tube member 36 become unobstructed for purposes of fluid infusion. Thus, if it is desired to infuse fluid into the bladder 74 as well as the ureter 72 and the renal cavity 70, the proximal end 44 of the guide tube member 36 can be located at the distal end 16 of the stent 12.

Since the openings 24 are provided in the stent 12 throughout the entire length of the stent, any fluid infused at the distal end 16 of the stent 12 would tend to disperse through openings 24 starting at the distal end 16 of the stent 12.

When fluid infusion is no longer desired in the stent 12 and there is a need for the stent to perform a drainage function, the guide tube member 36 can be completely removed from the patient by engaging the push catheter 64 against the distal end 16 of the stent while the guide tube member 36 is withdrawn. The stent 12 can thus be left as an indwelling member for drainage of fluid from the renal cavity 70 to the bladder 74. The openings 24 provided throughout the length of the stent 12 including openings 24 provided in the proximal and distal end portions 14 and 16, optimize the drainage function of the stent 12.

When it is desired to remove the stent 12 from the patient, withdrawal is easily accomplished by nonsurgical techniques using the sutures 34 which extend outwardly of the patient.

In some instances it may be desirable to infuse through a stent member that has no perforations therein. Thus infusion with the guide tube member will enable fluid to be directed into the stent member at any selected location.

Some advantages of the present invention evident from the foregoing description include an infusion stent system that directs fluid to any selected location within the stent through a guide tube member that is movable relative to the stent. The guide tube member has a multiplicity of functions serving as a guide for positioning of the stent in a patient, an infusion channel for passage of fluid to the stent and an adjustable bypass member to selectively obstruct drainage openings in the stent when infusion is required.

Installation of the infusion stent system is advantageously facilitated by use of a removable core member that can be selectively located in the guide tube member to selectively soften and stiffen the proximal tip of the guide tube member and aid in negotiation of the ureter during positioning of the stent. A further advantage of the infusion stent system is that the stent can function as an indwelling drainage member after infusion is completed, and will provide optimal drainage because of the presence of openings along the entire length of the stent.

In view of the above, it will be seen that the several objects of the present invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:
1. An infusion stent system comprising
 a. a flexible stent member of a first predetermined length, said stent member having a main body portion with a proximal end portion and a distal end portion,
 b. a hollow flexible guide tube member of a second predetermined length greater than said first prede- termined length, said guide tube member being infusible with fluid and receivable in said stent member such that said stent member and said guide tube member are relatively slidable with respect to each other, said guide tube member having a proximal end that is positionable in said stent member at any selected location within said stent member, such that when the proximal end of said guide tube member is at any said selected location in said stent member infusion of fluid through said guide tube member is directed outwardly of said guide tube member at any said selected location in said stent member, said guide tube member being removable from said stent member.

2. The infusion stent system as claimed in claim 1 wherein said guide tube member is substantially imperforate.

3. The infusion stent system as claimed in claim 1 wherein said guide tube member is formed of a fluorinated polymer.

4. The infusion stent system as claimed in claim 3 wherein said guide tube member is formed with a wire reinforcement.

5. The infusion stent system as claimed in claim 1 including a flexible core member of a third predetermined length greater than said second predetermined length, said core member being sized for slidable reception in said guide tube member, said core member including insertion limiting means nonreceivable in said guide tube member to limit insertion of said core member in said guide tube member.

6. The infusion stent system as claimed in claim 5 wherein said flexible core member has a proximal free end positionable in said guide tube member at any selected location within said guide tube member, said flexible core member being removable from said guide tube member.

7. The infusion stent system as claimed in claim 6 wherein said flexible core member has a terminal section of predetermined extent up to the proximal free end of said core member and a first substantially uniform cross section between said insertion limiting means and said terminal section, said terminal section having a reduced cross-section with respect to said first substantially uniform cross-section.

8. The infusion stent system a claimed in claim 7 wherein the proximal free end of said core member has an enlargement with a cross-sectional magnitude that is greater than the cross-sectional magnitude of said terminal section and approximately equivalent to the cross-sectional magnitude of said first substantially uniform cross-section.

9. The infusion stent system as claimed in claim 7 wherein the terminal section of said flexible core member is tapered toward the proximal free end of said core member to a minimum tapered cross-section, the proximal free end of said core member having an enlargement with a cross-sectional magnitude that is greater than the cross-sectional magnitude of said minimum tapered cross-section an approximately equivalent to the cross-sectional magnitude of said first substantially uniform cross-section.

10. The infusion stent system as claimed in claim 5 wherein said stent member has normally curved proximal and distal end portions, and wherein the flexibility of said guide tube member and said core member are selected such that said curved proximal and distal end portions are substantially straightened when said stent member is disposed on said guide tube member with said core member engaged in said guide tube member, the flexibility of said guide tube member permitting said normally curved proximal and distal end portions of said stent member to re-form when said core member is disengaged from the guide tube member at the area of disposition of said stent member on said guide tube member.

11. The infusion stent system as claimed in claim 2 including a hollow, tubular, flexible, push catheter member of a fourth predetermined length, said fourth predetermined length being of lesser magnitude than said third predetermined length, said push catheter member being sized for slidable engagement on said guide tube member and having a wall thickness that interferes with the distal end portion of said stent member to permit said push catheter to abut said distal end portion of said stent member such that movement of said push catheter member against said stent member causes said stent member to move along said guide tube member.

12. The infusion stent system as claimed in claim 2 wherein said stent member has a plurality of openings along the length thereof such that when the proximal end of said guide tube member is at any said selected location in said stent member infusion of fluid through said guide tube member is directed outwardly of said stent member through openings in said stent member beyond said selected location.

13. The infusion stent system as claimed in claim 2 wherein said stent member has a plurality of openings along the length thereof and wherein the proximal end of said guide tube member is positionable at the proximal end of said stent member to bypass selected said openings in said stent member up to the proximal end portion of said stent member and permit infusion of fluid outwardly of said stent member substantially only at openings in the proximal end portion of said stent member that are not bypassed by said guide tube member.

14. The infusion stent system as claimed in claim 2 wherein said stent member has a plurality of openings along the length thereof and wherein the proximal end portion of said guide tube member is positionable in said stent member intermediate said proximal and distal end portions of said stent member to bypass openings in said stent member up to the location of the proximal end portion of said guide tube member and permit infusion of fluid outwardly of said stent member substantially only at openings in said stent member that are not bypassed by said guide tube member.

15. An infusion stent system comprising
   a. a flexible hollow imperforate guide tube member having a proximal end with an infusion opening;
   b. a flexible hollow stent member slidable on said guide tube member;
   c. a flexible hollow push catheter member slidable on said guide tube member for pushing said stent member along said guide tube member to a predetermined position in the renal cavity, ureter and bladder, said push catheter member being removeable from said guide tube member, and
   d. said hollow flexible guide tube member being moveable relative to said stent member when said stent member is in said predetermined position, such that the proximal end of said guide tube member is positionable at selected predetermined locations in said stent member to permit infusion of fluid outwardly of said guide tube member at said selected predetermined locations in said stent member.

16. The infusion stent system as claimed in claim 15 wherein said stent member includes a plurality of perforations, the proximal end of said guide tube member being positionable at said selected predetermined locations in said stent member to bypass selected perforations in said stent member and permit infusion of fluid outwardly of said stent member substantially only at perforations in said stent member that are not bypassed by said guide tube member.

17. The infusion stent system as claimed in claim 15 further including a flexible core member slidably engageable in said guide tube member to selective positions within said guide tube member up to the proximal end of said guide tube member.

18. The infusion stent system as claimed in claim 17 wherein said core member has a terminal section and a main body section, said terminal section having a lesser cross-sectional magnitude than the main body section.

19. The infusion stent system as claimed in claim 18 wherein said terminal section has a free end with an enlargement of greater cross-sectional magnitude than said terminal section and lesser cross-sectional magnitude than said main body section.

20. A method of infusing fluid in the renal cavity comprising
   a. forming a flexible, hollow guide tube member with inlet and outlet openings,
   b. locating the guide tube member in the renal cavity, the ureter and the bladder,
   c. drawing a stent member onto the guide tube member,
   d. pushing the stent member along the guide tube member with a push catheter until the stent member is located in the renal cavity, the ureter and the bladder;
   e. moving the guide tube member relative to the stent member such that the outlet opening of the guide tube member is at a pre-selected location in the stent member, and
   f. infusing fluid through the inlet opening of the guide tube member for flow outwardly of the outlet opening of the guide tube member at the preselected location in the stent member.

21. The method of claim 20 including perforating the stent member along its entire length, and infusing fluid through the guide tube member for flow outwardly of the stent member at perforations in the stent member beyond the outlet opening of the guide tube member.

22. The method of claim 21 wherein the renal cavity is infused by locating the outlet opening of the guide tube member in a position in the stent member that bypasses the perforations in the stent member except the perforations that are proximal to the renal cavity, and infusing fluid through the guide tube member for passage through the stent member into the renal cavity.

23. The method of claim 21 wherein the ureter is infused by locating the outlet opening of the guide tube member in a position in the stent member that bypasses the perforations in the stent member up to the ureter and infusing fluid through the guide tube member for passage through the stent member into the ureter.

24. The method of claim 18 including inserting a non-tubular core member into the guide tube member during location of the guide tube member in the renal cavity, the ureter and the bladder, and maintaining the core member in the guide tube member until the stent member is also located in the renal cavity, the ureter and the bladder.

* * * * *